United States Patent [19]

Nakajima et al.

[11] Patent Number: 5,496,328
[45] Date of Patent: Mar. 5, 1996

[54] INSERTING DEVICE FOR DEFORMABLE INTRAOCULAR LENS

[75] Inventors: Toshiyuki Nakajima; Toshikazu Kikuchi, both of Tokyo, Japan

[73] Assignee: Canon Staar Co., Inc., Tokyo, Japan

[21] Appl. No.: 274,681

[22] Filed: Jul. 13, 1994

[30] Foreign Application Priority Data

Jul. 15, 1993  [JP]  Japan .................. 5-175332

[51] Int. Cl.⁶ .................................. A61B 17/00
[52] U.S. Cl. .................................... 606/107
[58] Field of Search .................. 606/1, 107, 108; 623/4, 6

[56] References Cited

U.S. PATENT DOCUMENTS

| 4,573,998 | 3/1986 | Mazzocco . | |
|---|---|---|---|
| 4,681,102 | 7/1987 | Bartell | 606/107 |
| 5,098,439 | 3/1992 | Hill et al. | 606/107 |
| 5,190,552 | 3/1993 | Kelman | 606/107 |

FOREIGN PATENT DOCUMENTS

| 5-58748 | 7/1983 | Japan . |
|---|---|---|
| 5-83253 | 8/1992 | Japan . |
| 5-103803 | 4/1993 | Japan . |
| 5-103808 | 4/1993 | Japan . |
| 5-103809 | 4/1993 | Japan . |

*Primary Examiner*—Stephen C. Pellegrino
*Assistant Examiner*—Glenn Dawson
*Attorney, Agent, or Firm*—Ladas & Parry

[57] ABSTRACT

An inserting device for inserting an intraocular lens into the eye. An interference preventing portion is formed in a lens holding section which is provided with an opening/closing mechanism and is a part of a holder member attached to a body. An intraocular lens is held by the lens holding section such that its optical part made of an elastic material is deformed into a smaller shape. The tip portion of a support which is made of a different material from that of the optical part and which extends backward the optical part is received by the interference preventions portion. When a pusher rod of a pusher mechanism attached to the body is advanced, only the optical part is pushed by the pusher rod without causing interference between the pusher rod and the tip portion of the support, thereby inserting the intraocular lens into the eye. Therefore, the intraocular lens held by the lens holding section can be pushed out by the pusher rod of the pusher mechanism and safely inserted into the eye without causing deformation of the supports of the intraocular lens.

16 Claims, 3 Drawing Sheets

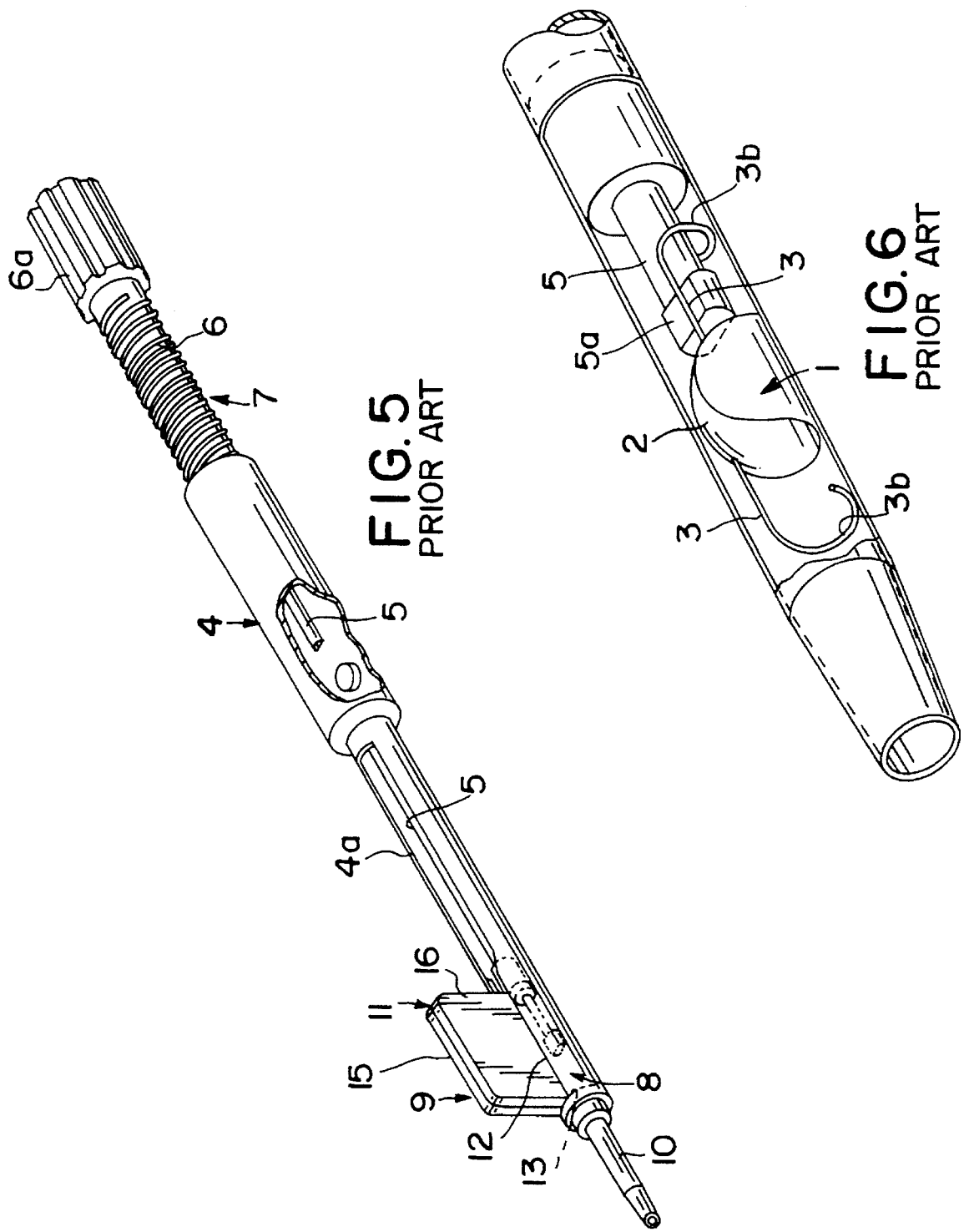

INSERTING DEVICE FOR DEFORMABLE INTRAOCULAR LENS

BACKGROUND OF THE INVENTION

1. Field of the Invention

The present invention relates to an inserting device for inserting a deformable intraocular lens into the eye in place of the natural lens when the latter is physically extracted because of cataracts, and particularly to an inserting device for a deformable intraocular lens which has an improved holder member for holding the deformable intraocular lens.

2. Description of the Related Art

It is generally accepted that when a cataract-impaired lens is surgically extracted, smaller incisions in the eyeball cause less chance of postoperative astigmatism.

Accordingly, a technique called KPE (Kelman's pharmacoemulsification; suction of lens substance crushed by ultrasonic emulsification) using an ultrasonic emulsification/suction apparatus has been developed. With this apparatus, an opaqued lens is crushed and emulsified by ultrasonication, and then sucked for removal. This technique permits an operation in which lenses are extracted through a small incision of approximately 4 mm, as compared to larger incisions of about 10 mm according to the conventional ECCE operation technique (extracapsular cataract extraction).

In connection with the technique which made small incisions possible as mentioned above, intraocular lenses which can be inserted through a small incision have been developed. Conventional intraocular lenses have an optical part made of a hard material such as glass or plastic, and therefore, the incisions prepared at the time of transplant are greater than the diameter of the optical part which are in most cases 6.5 mm or more. Accordingly, even though a lens is extracted through a small incision according to the KPE technique, it is necessary that the incision be enlarged when a hard intraocular lens is inserted.

To solve this problem, Japanese Patent Application No. 558-18005 (Japanese Patent Application Laid-open (kokai) No. 146346/1983, Japanese Patent Publication No. H5-58748) discloses a deformable intraocular lens which can be inserted through a small incision made in an eyeball.

As shown in FIG. 4 (Prior Art), such an intraocular lens 1 is composed of an optical part 2 made of an elastic material and having predetermined memory characteristics, and two symmetrically disposed supports 3 which hold the optical part within the eye. The supports 3 are made of a different material from the optical part 2, and the bases 3a of the supports 3 are embedded in the peripheral portion of the optical part 2 for fixing, while the wire-shaped tails 3b are curved.

The supports 3 are made of a material such as a synthetic resin having a sufficient hardness and the wire-shaped tails 3b extending from the optical part 2 have a spring function so that the optical part 2 is stably placed in the eye on the optical axis even when the lens 1 receives force such as compression stress within the eye.

An inserting device for deformable intraocular lenses has been proposed as described in Japanese Patent Application No. H3-142067 Japanese Patent Application Laid open (kokai) No. H5-103803). As shown in FIG. 5 and FIG. 6, the inserting device is composed of a cylindrical body 4 provided with a receiving opening 4a having a narrowed portion at its forward end portion; a pusher mechanism 7 provided with a pusher rod 5 inserted into the body 4, and a male-screw sleeve 6 which is screw-engaged with a female screw of the body 4 for advancing and retracting the pusher rod 5; and a holder member 11 provided with a lens holding section 9 having an opening/closing mechanism 8, and a tubular insertion tip 10 formed at the front side of the lens holding section 9.

In the lens holding section 9, a stationary half sleeve 12 is integrally formed with the rear end of the insertion tip 10, and a movable half sleeve 13 facing the stationary half sleeve 12 is provided near the rear end of the insertion tip 10. The lower edge of the movable half sleeve 13 is joined with the stationary half sleeve 12 through an unillustrated hinge for opening and closing operations. Stationary and movable pressing flanges 15 and 16 are projected from the upper edges of the stationary and movable half sleeves 12 and 13.

When the opening/closing mechanism 8 composed of the movable half sleeve 13, the hinge portion and the movable pressing flange 16 is closed, the movable pressing flange 16 contacts the stationary plate 15 so that the movable half sleeve 13 contacts the stationary half sleeve 12, thereby forming a tubular shape which is aligned with the insertion tip 10.

When the deformable intraocular lens 1 is inserted into the eye in place of the natural lens using the above-described conventional inserting device, the holder member 11 is taken out from the body 4 and the opening/closing mechanism 8 is then opened. The intraocular lens 1 is placed on the lens holding section 9 of the holder member 11. Subsequently, the opening/closing mechanism 8 is closed so that the intraocular lens 1 is deformed into a smaller shape. While maintaining this state, a major part of the holder member 11 excepting the pressing flanges 15 and 16 is inserted into the front portion of the body 4 through the receiving opening 4a so that the pressing flanges 15 and 16 are projected upward from the receiving opening 4a.

The holder member 11 is subsequently advanced to insert the pressing flanges 15 and 16 into the narrowed portion of the receiving opening 4a so that the opening/closing mechanism 8 is maintained closed, and the insertion tip 10 is projected from the forward end of the body 4. In this way, the assembly of the inserting device is carried out.

After the assembly of the inserting device, the insertion tip 10 of the holder member 11 is inserted into the eye through a small incision of about 4 mm formed in the eye ball. A cylindrical operation sleeve 6a formed at the rear end of the male-screw sleeve 6 of the pusher mechanism 7 is then rotated to advance the pusher rod 5 from its retracted position. With this operation, the forward end of the pusher rod 5 contacts the intraocular lens 1 to push out the intraocular lens 1 from the lens holding section 9 of the holder member 11 through the insertion tip 10 so that the intraocular lens 1 is inserted into the eye through the small incision. The optical part 2 of the intraocular lens 1 is restored from the small deformed shape to the original large shape according to the shape memorizing characteristics of the lens. As described above, the insertion of an intraocular lens through a small incision is realized by the improvements in both the intraocular lens and the insertion apparatus.

In the conventional insertion apparatus, the body 4, the pusher rod 5 of the pusher mechanism 7 and the male-screw sleeve 6 are made of a metallic material, and the holder member 11 is integrally made of a flexible synthetic resin.

In the conventional inserting device for intraocular lenses, when the pusher rod is advanced by an operation of the pusher mechanism while an intraocular lens has been deformed in a smaller shape and held by the lens holding section of the holder member, the pusher rod interferes with a support extending from the rear side (the side corresponding to the rear end of the holder member) of the optical portion of the intraocular lens at the beginning of the push-out operation, so that the support receives external force directly form the pusher rod. Since the support is made of a hard material having a spring function as described above, the support has a chance to be permanently deformed, thereby causing a problem that the optical part cannot be supported at a predetermined position within the eye, and the original function of the support deteriorates.

Therefore, as shown in FIG. 6, the pusher rod 5 is provided at its forward end with a push-out portion 5a whose upper and lower portions are cut away so as to prevent the pusher rod 5 from interfering with the support 3 of the intraocular lens 1. However, in the case where the intraocular lens 1 is incorrectly held in the holder member 11, for example, the position of the intraocular lens 1 deviates from the desired position, the push-out portion 5a interferes with the support 3.

SUMMARY OF THE INVENTION

The present invention is to solve the above-mentioned problems and to provide an inserting device for deformable intraocular lenses which is capable of preventing a pusher rod from interfering with a support of an intraocular lens held by a lens holding portion of a holder member at the beginning of a push-out operation, thereby permitting the intraocular lens to be inserted into the eye without deforming the support.

According to the present invention, there is provided an inserting device for a deformable intraocular lens having an optical part which is made of an elastic material and which has predetermined memory characteristics, and a plurality of supports which are made of a flexible material different from that of the optical part and which support the optical part in the eye. The inserting device includes a holder member having a lens holding section with an opening/closing mechanism for deforming a deformable intraocular lens in a small shape and holding it in the lens holding section, a pusher mechanism for pushing out the intraocular lens held by the lens holding section into the eye by a pusher rod, and a body to which the pusher mechanism is attached. The inserting device is further provided with an interference preventing portion formed in the lens holding section which has the opening/closing mechanism and is a part of the holder member so as to prevent interference between the support of the intraocular lens and the pusher rod.

In the inserting device according to the present invention, an intraocular lens is placed on the lens holding section of the holder member in the state where the opening/closing mechanism is opened. Then, the opening/closing mechanism is closed to deform the optical part of the intraocular lens into a smaller shape and to hold the lens in the lens holding section. In this state, the tip portion or the tail of the support backwardly extending from the rear side of the optical part of the intraocular lens enters the interference preventing portion formed in the lens holding section. Therefore, the pusher rod can push the optical part without contacting the support even at the beginning of a push-out operation in which the intraocular lens is pushed out by the pusher rod of the pusher mechanism.

Accordingly, it is possible to prevent the backwardly extending support from being deformed by the pusher rod, or from receiving force from the pusher rod, thereby preventing the function of the supports from deteriorating due to the deformation of the support. Therefore, it is possible to eliminate the fear that the intraocular lens having a deformed support is inserted into the eye. This increase the safety of the insertion operation of the intraocular lens.

BRIEF DESCRIPTION OF THE DRAWINGS

FIG. 5 (Prior Art) is a perspective view showing a conventional inserting device for deformable intraocular lenses; and FIG. 6 (Prior Art) is a partially sectioned perspective view of the front portion of the inserting device shown in FIG. 5.

DESCRIPTION OF THE PREFERRED EMBODIMENT

An embodiment of the present invention will be described while referring to FIGS. 1 through 3.

Figure 1:
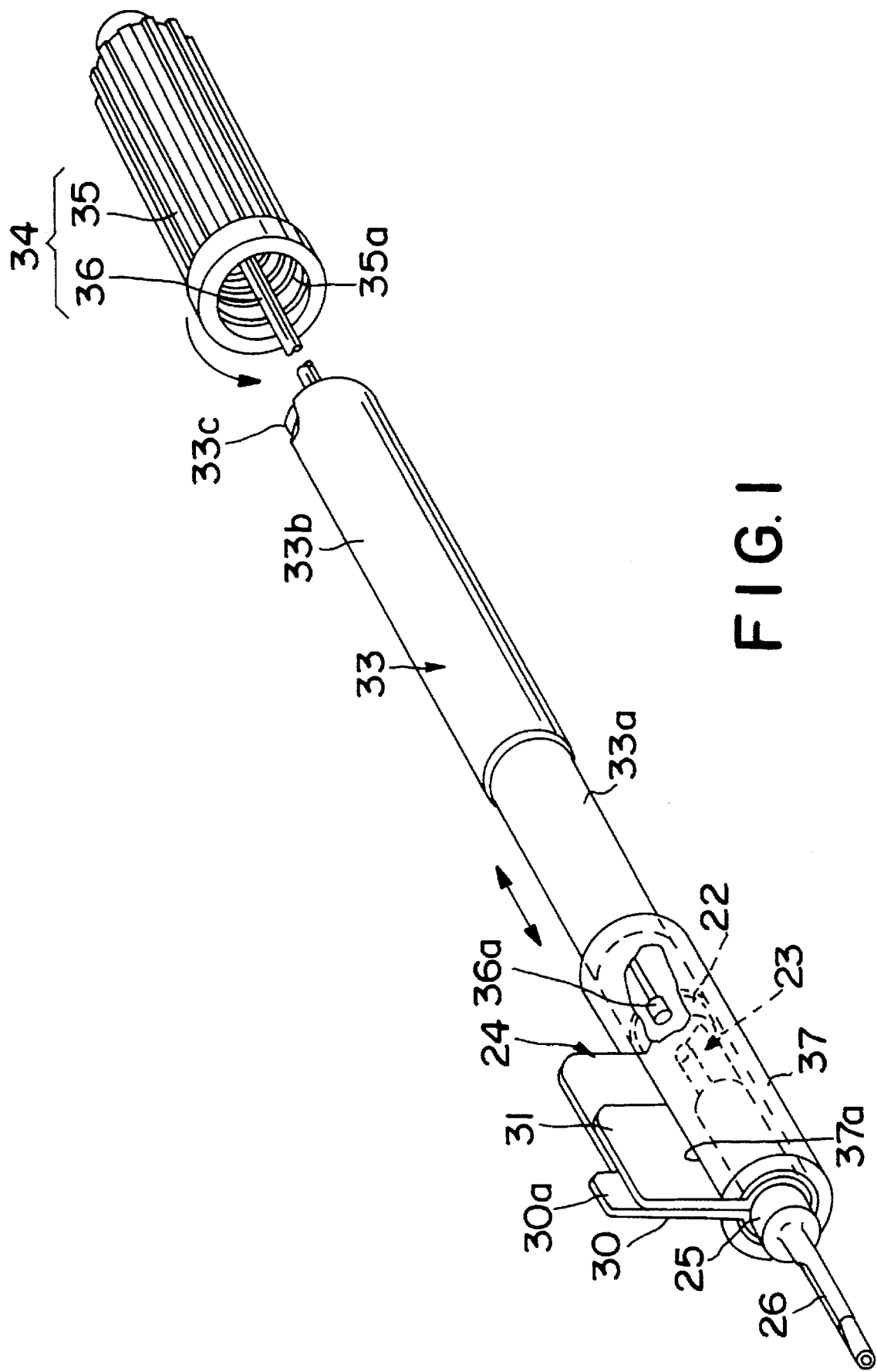
FIG. 1 is a partially sectioned perspective view showing an inserting device for deformable intraocular lenses according to an embodiment of the present invention.
Figure 2:
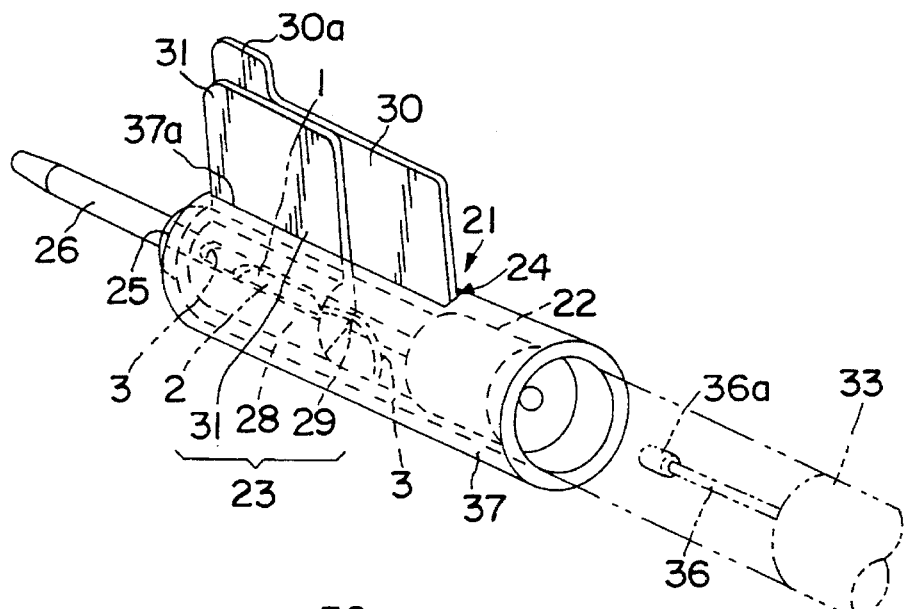
FIG. 2 is a perspective view of a forward portion of the inserting device shown in FIG. 1.
Figure 3:
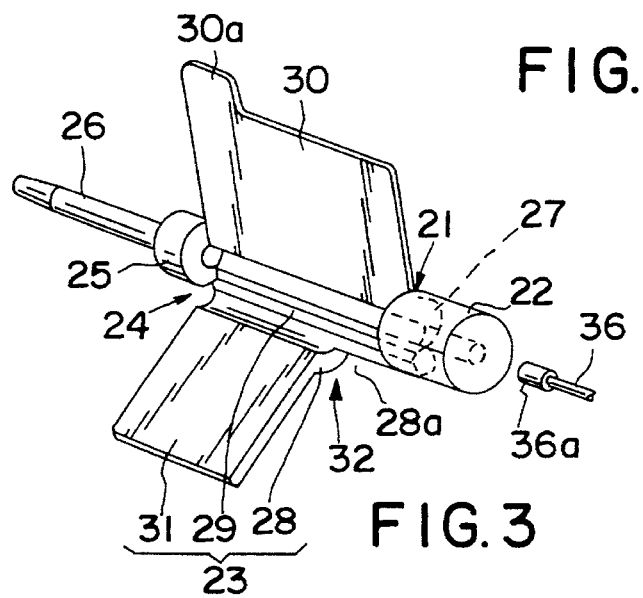
FIG. 3 is a perspective view of a holder member of the inserting device shown in FIG. 1.

In FIGS. 1, 2 and 3, numeral 21 denotes a holder member. The holder member 21 is composed of a rear cylindrical portion 22, a lens holding section 24 having an opening/closing mechanism 23 and formed at the front side of the rear cylindrical portion 22, and a front cylindrical portion 25 provided at the front side of the lens holding section 24. A tapered off insertion tip 26 is projected from the front end of the front cylindrical portion 25. These portions are aligned to have a common center axis.

The lens holding section 24 is composed of a stationary half sleeve 27 integrally formed with the rear cylindrical portion 22 and the front cylindrical portion 25 to be located therebetween, and a movable half sleeve 28 facing the stationary half sleeve 27 and located between the rear cylindrical portion 22 and the front cylindrical portion 25. The lower edge of the movable half sleeve 28 is joined with the lower edge of the stationary half sleeve 27 through a hinge 29 for opening/closing operations.

Stationary and movable pressing flanges 30 and 31 are projected from the upper edges of the stationary and movable half sleeves 27 and 28. A projection 30a is formed on the upper edge of the stationary pressing flange 30 at its front side. Also, a cut-away portion 28a is formed above the rear portion of the movable half sleeve 28. The movable pressing flange 31 is formed only in a region on the front side of the cut-away portion to form an interference preventing portion 32 for preventing interference between supports 3 of an intraocular lens 1 and a pusher rod 36 which will be described later.

When the opening/closing mechanism 23 composed of the movable half sleeve 28, the hinge 29 and the movable pressing flange 31 is closed, the movable pressing flange 31 contacts the stationary pressing plate 30 so that the movable half sleeve 28 contacts the stationary half sleeve 27, thereby forming a tubular shape which is aligned with the rear cylindrical portion 22 and the front cylindrical portion 25.

The rear cylindrical portion 22 of the holder member 21 is coaxially fixed to the front portion 33a of a body 33, which will be described layer, for example, by tight insertion of the rear cylindrical portion 22 into the front portion 33a. The body 33 has a cylindrical shape formed by the front portion 33a and the rear portion 33b having a diameter larger than that of the front portion 33a.

A male screw 33c is formed on the peripheral surface of the rear portion 33b of the body 33 in a small range. The male screw 33c is engaged with a female screw 35a formed on the inner surface of an operation sleeve 35 of a pusher mechanism 34. The pusher mechanism 34 is provided with a pusher rod 36 whose rear end portion is coaxially inserted into the operation sleeve 35 to be supported by the operation sleeve 35. With this, the pusher rod 36 is allowed to rotate relative to the operation sleeve 35 but is prevented from axially moving relative to the operation sleeve 35. The front portion of the pusher rod 36 is coaxially inserted into the body 33 and is extended toward the front side of the body 33. The pusher rod 36 is prevented from rotating relative to the body by unillustrated proper means. Also, a push-out portion 36a having a large diameter is formed at the tip of the pusher rod 36. The back end of the operation sleeve 35 is closed by a suitable means.

The front portion 33a of the body 33 and the rear cylindrical portion 22 of the holder member 21 have a common center axis and form a continuous outer cylindrical surface. These portions 33a and 22 are slidably fitted into a transparent engagement member 37 while relative rotation between the portions 33a and 22 and the engagement member 37 is prohibited. An engagement groove 37a is formed in the front upper portion Of the engagement member 37 to extend in the axial direction. When the engagement member 37 is advanced to its advanced position, the engagement groove 37a engages the stationary and movable pressing flanges 30 and 31 of the holder member 21 to cause them to contact each other, thereby maintaining the opening/closing mechanism 23 closed. When the engagement member 37 is retracted, the engagement groove 37a is separated from the pressing flanges 30 and 31 to open the opening/closing mechanism 23.

The holder member 21 is integrally made of a flexible synthetic resin, while the body 33, the operation sleeve 35, the pusher rod 36 and the engagement member 37 are made of a synthetic resin, respectively.

Figure 4:
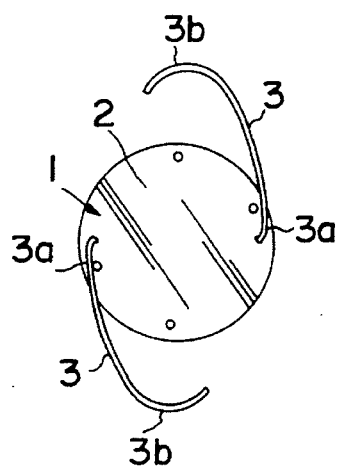
FIG. 4 (Prior Art) is an enlarged front view showing an example of a deformable intraocular lens.

When the deformable intraocular lens 1 shown in FIG. 4 is inserted into the eye using the inserting device according to the present embodiment, the pusher rod 36 of the pusher mechanism 34 and the cylindrical engagement portion 37 are retracted so that the opening/closing mechanism 23 of the holder member 21 is brought into an open state in which the movable pressing flange 31 and the movable half sleeve 28 are opened. In this state, the intraocular lens 1 is placed on the lens holding section 24 such that the optical part 2 of the intraocular lens 1 is located above the hinge 29, one of the support 3 is located near the stationary half sleeve 27 and extends in a forward direction, and the other support 3 is located near the movable half sleeve 28 and extends in a backward direction.

Subsequently, the opening/closing mechanism 23 is closed so that the movable pressing flange 31 and the movable half sleeve 28 abut on the stationary pressing flange 30 and the stationary half sleeve 27, respectively. With this operation, the intraocular lens 1 is held by the lens holding section 24 such that the optical part 2 is folded in two by the movable and stationary half sleeves 28 and 27 to have a curved smaller shape.

While maintaining this state, the engagement member 37 is advanced to engage the engagement groove 37a with the stationary and movable pressing flanges 30 and 31 so as to maintain the closed state. Subsequently, the insertion tip 26 of the holder member 21 is inserted into the eye through a small incision of about 4 mm through which the natural lens has been extruded. Then, the operation sleeve 35 of the pusher mechanism 34 is manually rotated in the forward direction so that the pusher rod 36 is advanced together with the operation sleeve 35 due to the screw-engagement between the female screw 35a of the operation sleeve 35 and the male screw 33c of the body 33. As the pusher rod 36 moves forward, the push-out portion 36a thereof contacts the optical part 2 of the intraocular lens 1 and pushes the same so that the intraocular lens 1 is pushed out from the inserting device through the front cylindrical portion 25 and the insertion tip 26, and is inserted into the eye through the small incision.

Since the forward end of the insertion tip 26 has entered inside of the eye through the incision, the optical part 2 of the intraocular lens 1 ejected from the insertion tip 26 restores the original large shape due to the elastic restoring force based on the memory characteristics, and is supported by the supports 3 within the eye, thereby completing the implantation of the intraocular lens 1.

It is preferred that the intraocular lens 1 be pushed out together with a lubricant for smooth advancement of the intraocular lens 1 within the insertion tip 26.

In the inserting device according to the present invention, the cut-away portion 28a is formed above the rear end portion of the movable half sleeve 28 of the opening/closing mechanism 23 provided in the lens holding section 24, and the movable pressing flange 31 is not formed in the area above the cut-away portion 28a so as to form the interference preventing portion 32. Therefore, in the state where the intraocular lens 1 is held by the lens holding section 24, the curved tip portion or tail 3b of the support 3 backwardly projecting from the optical part 2 of the intraocular lens 1 enters the interference preventing portion 32. Accordingly, it is possible to push out the optical part 2 and insert the same into the eye without deforming the backwardly extending support 3 at the beginning of the push-out operation in which the optical section 2 is pushed out by the push-out portion 36a of the pusher rod 36. Therefore, the optical part 2 can be safely supported by the supports 3 at a predetermined position.

In the inserting device according to the present embodiment, since the cylindrical engagement member 37 is made of a transparent synthetic resin, the opening/closing mechanism 23 or the like can be seen through the engagement member 37 when the intraocular lens 1 is put into the lens holding section 24. This allows a user to check the conditions of the intraocular lens 1 in the lens holding section 24, thereby increasing the safety.

In the inserting device according to the present embodiment, since the holder member 21, the body 33, the operation sleeve 35, the pusher rod 36 and the engagement member 37, which constitute the inserting device, are made of a synthetic resin, the inserting device can be manufactured at low costs, and can be disposable.

The engagement member does not necessarily have a cylindrical shape. A tubular member having a groove formed in the lower side of the member and extending over the entire length thereof may be used as an engagement member. In such a case, the engagement member is attached to the forward portion of the body by elastically deforming the engagement member. In this case, the body and the holder member may be integrally formed.

In the above-described embodiment, although the holder member is fixed to the forward end of the body, the holder member may be used without being fixed. Namely, the holder member 21 shown in FIG. 3 may be used as the holder member 11 shown in FIG. 5 and FIG. 6. In such a case, the holder member 21 is detachably inserted into the forward end of the body 4 though the receiving opening 4a. In this case, the rear cylindrical portion of the holder member 21 may be omitted.

Moreover, in the present invention, the interference preventing portion may be provided by forming outwardly expanded curved sections at the rear ends of the movable half sleeve and the movable pressing flange provided in the opening/closing mechanism of the holder member.

What is claimed is:

1. An apparatus for inserting a deformable intraocular lens into an eye, the lens having an optical part made of an elastic material with predetermined memory characteristics, the lens having a plurality of flexible supports made of a material different than the elastic material, the apparatus comprising:

(a) a body;

(b) first and second half sleeves connected to each other, at least one of the half sleeves being connected to the body, at least one of the half sleeves being movable relative to the other half sleeve, each half sleeve having a proximal end and a distal end, the proximal end being closer to the body than the distal end, the first and second half sleeves defining a lens-receiving portion for receiving the lens when the half sleeves are open, the first and second half sleeves defining a tube when the half sleeves are closed, the tube having an open proximal end and an open distal end, the proximal end of the tube communicating with the distal end of the tube by a bore, the bore communicating with the body, the first and second half sleeves are adapted to fold the lens inside the bore when the half sleeves are closed, the proximal end of the tube being closer to the body than the distal end of the tube, the proximal end of the tube being farther from the body than the proximal end of the second half sleeve when the half sleeves are closed, the first half sleeve having a cutaway portion located between the proximal end of the tube and the proximal end of the first half sleeve, the proximal end of the tube being open to allow a portion of at least one lens support to protrude through the proximal end of the tube and into the cutaway portion when the lens is folded in the bore;

(c) an insertion tip, the insertion tip having a proximal end and a distal end, the proximal end of the insertion tip being closer to the body than the distal end of the insertion tip, the proximal end of the insertion tip being connected to the distal end of at least one of the half sleeves, the proximal end of the insertion tip communicating with the distal end of the insertion tip by a lumen, the lumen communicating with the bore; and (d) a pusher rod disposed in the body, the pusher rod in use being inserted into the proximal end of the tube to push the folded lens through the bore, out of the distal end of the tube, through the lumen, out of the distal end of the insertion tip, and into the eye without permanently deforming the protruding lens support.

2. An apparatus as claimed in claim 1, wherein a first flange is connected to the first half sleeve and a second flange is connected to the second half sleeve, the first flange being adjacent to the second flange when the half sleeves are closed, each flange having a proximal end and a distal end, the proximal end of the first flange being closer to the body than the distal end of the first flange, the proximal end of the second flange being closer to the body than the distal end of the second flange, the proximal end of the first flange being farther from the body than the proximal end of the second flange when the half sleeves are closed, the first flange being shorter than the second flange, whereby an interference-preventing means is formed for receiving a portion of the protruding lens support when the half sleeves are closed.

3. An apparatus as claimed in claim 2, wherein the first and second half sleeves are articulated, and wherein the pusher rod is rotatably fixed relative to the body.

4. An apparatus as claimed in claim 3, further comprising:

a transparent engagement member for holding the first and second half sleeves closed to define the tube when a portion of the engagement member is advanced over a portion of the first and second half sleeves, the engagement member having an engagement groove for holding the first flange adjacent to the second flange when the first and second half sleeves are closed.

5. An apparatus as claimed in claim 2, further comprising:

a transparent engagement member for holding the first and second half sleeves closed to define the tube when a portion of the engagement member is advanced over a portion of the first and second half sleeves, the engagement member having an engagement groove for holding the first flange adjacent to the second flange when the first and second half sleeves are closed.

6. An apparatus as claimed in claim 1, wherein the first and second half sleeves are articulated, and wherein the pusher rod is rotatably fixed relative to the body.

7. An apparatus as claimed in claim 6, further comprising:

a transparent engagement member for holding the first and second half sleeves closed to define the tube when a portion of the engagement member is advanced over a portion of the first and second half sleeves.

8. An apparatus as claimed in claim 1, further comprising:

a transparent engagement member for holding the first and second half sleeves closed to define the tube when a portion of the engagement member is advanced over a portion of the first and second half sleeves.

9. An apparatus for inserting a deformable intraocular lens into an eye, the lens having an optical part made of an elastic material with predetermined memory characteristics, the lens having a plurality of flexible supports made of a material different than the elastic material, the apparatus comprising:

(a) a body;

(b) first and second half sleeves connected to each other, at least one of the half sleeves being connected to the body, at least one of the half sleeves being movable relative to the other half sleeve, each half sleeve having a proximal end and a distal end, the proximal end being closer to the body than the distal end, the first and second half sleeves defining a lens-receiving portion for receiving the lens when the half sleeves are open, the first and second half sleeves defining a tube when the half sleeves are closed, the tube having an open proximal end and an open distal end, the proximal end of the tube communicating with the distal end of the tube by a bore, the bore communicating with the body, the first and second half sleeves adapted to fold the lens inside the bore when the half sleeves are closed, the proximal end of the tube being closer to the body than the distal end of the tube, the proximal end of the tube being farther from the body than the proximal end of the second half sleeve when the half sleeves are closed, the first half sleeve having a cutaway portion located between the proximal end of the tube and the proximal end of the first half sleeve, the proximal end of the tube being open to allow a portion of at least one lens support to protrude through the proximal end of the tube and into the cutaway portion when the lens is folded in the bore; and (c) a pusher rod disposed in the body, the pusher rod in use being inserted into the proximal end of the tube to push the folded lens through the bore and out of the distal end of the tube into the eye without permanently deforming the protruding lens support.

10. An apparatus as claimed in claim 9, wherein a first flange is connected to the first half sleeve and a second flange is connected to the second half sleeve, the first flange being adjacent to the second flange when the half sleeves are closed, each flange having a proximal end and a distal end, the proximal end of the first flange being closer to the body than the distal end of the first flange, the proximal end of the second flange being closer to the body than the distal end of the second flange, the proximal end of the first flange being farther from the body than the proximal end of the second flange when the half sleeves are closed, the first flange being shorter than the second flange, whereby an interference-preventing means is formed for receiving a portion of the protruding lens support when the half sleeves are closed.

11. An apparatus as claimed in claim 10, wherein the first and second half sleeves are articulated, and wherein the pusher rod is rotatably fixed relative to the body.

12. An apparatus as claimed in claim 11, further comprising:

a transparent engagement member for holding the first and second half sleeves closed to define the tube when a portion of the engagement member is advanced over a portion of the first and second half sleeves, the engagement member having an engagement groove for holding the first flange adjacent to the second flange when the first and second half sleeves are closed.

13. An apparatus as claimed in claim 10, further comprising:

a transparent engagement member for holding the first and second half sleeves closed to define the tube when a portion of the engagement member is advanced over a portion of the first and second half sleeves, the engagement member having an engagement groove for holding the first flange adjacent to the second flange when the first and second half sleeves are closed.

14. An apparatus as claimed in claim 9, wherein the first and second half sleeves are articulated, and wherein the pusher rod is rotatably fixed relative to the body.

15. An apparatus as claimed in claim 14, further comprising:

a transparent engagement member for holding the first and second half sleeves closed to define the tube when a portion of the engagement member is advanced over a portion of the first and second half sleeves.

16. An apparatus as claimed in claim 9, further comprising:

a transparent engagement member for holding the first and second half sleeves closed to define the tube when a portion of the engagement member is advanced over a portion of the first and second half sleeves.

* * * * *